United States Patent
McDaniel et al.

(10) Patent No.: US 11,660,016 B2
(45) Date of Patent: May 30, 2023

(54) SINGLE-SIDED 3D MAGNET AND MAGNETIC RESONANCE IMAGING (MRI) SYSTEM

(71) Applicant: THE GENERAL HOSPITAL CORPORATION, Boston, MA (US)

(72) Inventors: Patrick McDaniel, Cambridge, MA (US); Lawrence L. Wald, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 303 days.

(21) Appl. No.: 16/833,052

(22) Filed: Mar. 27, 2020

(65) Prior Publication Data

US 2020/0305758 A1    Oct. 1, 2020

Related U.S. Application Data

(60) Provisional application No. 62/824,572, filed on Mar. 27, 2019.

(51) Int. Cl.
*A61B 5/055*    (2006.01)
*G01R 33/48*    (2006.01)
*G01R 33/24*    (2006.01)

(52) U.S. Cl.
CPC ............ *A61B 5/055* (2013.01); *G01R 33/246* (2013.01); *G01R 33/48* (2013.01)

(58) Field of Classification Search
USPC ....................................................... 600/410
See application file for complete search history.

(56) References Cited

U.S. PATENT DOCUMENTS

2006/0084857 A1*  4/2006  Massengill ............ G01R 33/28
                                                600/407
2019/0269330 A1*  9/2019  Gou ....................... A61B 5/055

OTHER PUBLICATIONS

Bashyam et al., Design and Experimental Validation of Unilateral Linear Halbach Magnet Arrays for Single-Sided Magnetic Resonance, Journal of Magnetic Resonance, 2018, 292:36-43.

Chen et al., Design and Analysis of the Novel Test Tube Magnet as a Device for Portable Nuclear Magnetic Resonance, IEEE Transactions on Magnetics, 2007, 43(9):3555-3557.

Cooley et al., Design of Sparse Halbach Magnet Arrays for Portable MRI Using a Genetic Algorithm, IEEE Transactions on Magnetics, 2018, 54(1):1-12.

Danieli et al., Single-Sided Magnetic Resonance Profiling in Biological and Materials Science, Journal of Magnetic Resonance, 2013, 229:142-154.

Eidmann et al., The NMR MOUSE, A Mobile Universal Surface Explorer, Journal of Magnetic Resonance, Series A, 1996, 122(1):104-109.

(Continued)

*Primary Examiner* — Rodney E Fuller
(74) *Attorney, Agent, or Firm* — Quarles & Brady LLP

(57) ABSTRACT

A magnet assembly for a portable magnetic resonance imaging (MRI) system includes a former having a plurality of slots and a plurality of magnet blocks configured to create a single-sided permanent magnet. Each of the plurality of magnet blocks are positioned in one of the plurality of slots of the former. The arrangement of the plurality of magnet blocks is configured to optimize homogeneity over a target field of view for brain imaging and to form a cap-shaped configuration to be positioned on a head of a subject.

18 Claims, 19 Drawing Sheets

(56) References Cited

OTHER PUBLICATIONS

Geethanath et al., Accessible Magnetic Resonance Imaging: A Review, Journal of Magnetic Resonance Imaging, 2019, 49(7):e65-e77.
Goga et al., Surface UV Aging of Elastomers Investigated with Microscopic Resolution by Single-Sided NMR, Journal of Magnetic Resonance, 2008, 192(1):1-7.
Halbach, Design of Permanent Multipole Magnets with Oriented Rare Earth Cobalt Materials, Nuclear Instruments and Methods, 1980, 169(1):1-10.
Jackson, Remote NMR Well Logging, Geophysics, 1981, 46:415.
Judeinstein et al., Low-Field Single-Sided NMR for One-Shot 1D-Mapping: Application to Membranes, Journal of Magnetic Resonance, 2017, 277:25-29.
Leupold et al., Novel High-Field Permanent-Magnet Flux Sources, IEEE Transactions on Magnetics, 1987, 23(5):3628-3629.
Li et al., 1H Nuclear Magnetic Resonance (NMR) as a Tool to Measure Dehydration in Mice, NMR in Biomedicine, 2015, 28(8):1031-1039.
Marques et al., Low-Field MRI: An MR Physics Perspective, Journal of Magnetic Resonance Imaging, 2019, 49(6):1528-1542.
Perlo et al., 3D Imaging with a Single-Sided Sensor: An Open Tomograph, Journal of Magnetic Resonance, 2004, 166(2):228-235.
Raich et al., Design and Construction of a Dipolar Halbach Array with a Homogeneous Field from Identical Bar Magnets: NMR Mandhalas, Concepts in Magnetic Resonance Part B: Magnetic Resonance Engineering, 2004, 23(1):16-25.
Tourell et al., T1-based Sensing of Mammographic Density Using Single-Sided Portable NMR, Magnetic Resonance in Medicine, 2018, 80(3):1243-1251.
Turek et al., Magnetic Field Homogeneity Perturbations in Finite Halbach Dipole Magnets, Journal of Magnetic Resonance, 2014, 238:52-62.
Van Landeghem et al., Low-Gradient Single-Sided NMR Sensor for One-Shot Profiling of Human Skin, Journal of Magnetic Resonance, 2012, 215:74-84.
Xu et al., Detection of Virgin Olive Oil Adulteration Using Low Field Unilateral NMR, Sensors, 2014, 14(2):2028-2035.

\* cited by examiner

SINGLE-SIDED 3D MAGNET AND MAGNETIC RESONANCE IMAGING (MRI) SYSTEM

CROSS-REFERENCE TO RELATED APPLICATIONS

This application is based on, claims priority to, and incorporates herein by reference in its entirety U.S. Ser. No. 62/824,572 filed Mar. 27, 2019, and entitled "Single-Sided 3D Magnetic Resonance Imaging (MRI) System."

STATEMENT REGARDING FEDERALLY SPONSORED RESEARCH OR DEVELOPMENT

This technology was made with government support under grants NIH R01EB018976, NIH R00EB021349, and NIH 5T32EB1680, awarded by the National Institutes of Health. The government has certain rights in the technology.

FIELD

The present disclosure relates generally to magnetic resonance imaging (MRI) systems and in particular, to portable MRI systems for obtaining MR images of the brain.

BACKGROUND

MRI has become a routine part of clinical medicine, especially for neuroimaging. Despite its, widespread clinical utility, size, expense, and siting requirements impose limitations on how conventional MRI scanners can be used within the health-care system. For example, the size, expense, and siting requirements prohibit the use of conventional MRI systems as point-of-care or monitoring devices. Installation of a while-body MR scanner or even a head-only type device using a conventional superconducting magnet entails a dedicated space, special infrastructure and safety requirements, such as a 5-Gauss exclusion area, high-power electrical supply, cooling system and shielded room. These prerequisites preclude the use of MRI in many settings, such as rural or developing world clinics that might not possess the required infrastructure. Furthermore, prior to receiving an MR scan, a patient must undergo a screening process, be transported to the scanner, and be moved into the magnet on a specialized patient table. In general, the nature of the full-sized MRI scanner requires the scanner to be operated at a central facility within the healthcare center whereby the patient is brought to the MRI and not vice-versa Together these requirements also preclude the used of MRI in time-sensitive situations or intensive-care settings where a patient cannot be transported from the point-of-care setting. The cost and dedicated centralized nature of current MRI facilities also prevents MRI from being used for continuous monitoring of a patient. While the high-quality, versatile but immobile nature of current MRI scanner configurations is well suited to the model with which they are used, it limits the reach of MRI.

Recent efforts have examined the development of portable and low-cost MRI systems for brain imaging. These include ultra-low field systems which attempt to reduce cost and weight by reducing $B_0$ below 10 mT, prepolarized systems, low field systems employing resistive magnets or permanent magnet arrays, potentially employing built-in encoding fields, and high field systems with reduced cryogen use or new superconductor or cryostat technology. Portable MRI systems have also been developed for extremity imaging and have found applications in musculoskeletal (MSK) imaging. Even smaller and more portable MR systems can be seen in the field of "single-sided" NMR system. Single-sided NMR systems have been designed for use in chemical analytics, petrology, and food science and allow the sample under test to be placed in a sensitive region outside of the device. The use of such ultra-portable "single-sided" spectrometers and relaxometers has been explored for medical applications, such as for skin profiling, mammographic, and hydration monitoring applications. These single-sided systems are far smaller than traditional MR scanners where the patient is interior to the magnet and thus have the potential to be true "point-of-care" devices. Prior efforts have also demonstrated imaging with a single-sided MR magnet. However, this device was had a steep (2.5 T/m) gradient extending away from the single sided magnet. This steep field drop-off required coil re-tuning at different depths, limited the depth penetration and potentially introduced strong diffusion dephasing. A larger 3D volumetric sensitive region with a gentler field drop-off would be desirable for brain applications.

Therefore, there is a need for a system and method for MRI that is portable, easily sited and low cost and may be used for rural, developing world and bedside settings.

SUMMARY

In accordance with an embodiment, a magnet assembly for a portable magnetic resonance imaging (MRI) system includes a former having a plurality of slots and a plurality of magnet blocks configured to create a single-sided permanent magnet. Each of the plurality of magnet blocks are positioned in one of the plurality of slots of the former and the arrangement of the plurality of magnet blocks is configured to optimize homogeneity over a target field of view for brain imaging and to form a cap-shaped configuration to be positioned on a head of a subject.

In accordance with another embodiment, a portable magnetic resonance imaging (MRI) assembly includes a magnet assembly comprising a plurality of magnet blocks configured to create a single-sided permanent magnet. The magnet assembly has an inner surface and an outer surface and the arrangement of the plurality of magnet blocks is configured to optimize homogeneity over a target field of view for brain imaging and to form a cap-shaped configuration to be positioned on a head of a subject. The portable MRI system also includes a set of gradient coils disposed around the outer surface of the magnet assembly and having a cap-shaped configuration and an RF coil disposed inside the inner surface of the magnet assembly and having a cap-shaped configuration.

BRIEF DESCRIPTION OF THE DRAWINGS

The present disclosure will hereafter be described with reference to the accompanying drawings, wherein like reference numerals denote like elements.

DETAILED DESCRIPTION

The present disclosure describes a single-sided magnet and MRI system that are portable, lightweight and low cost and may be used as a point-of care MRI device. The portable MRI system may be placed next to a patient during operation and, unlike conventional MRI systems, does not require the patient to be transported from a hospital bed to the MRI system and moved into the magnet of the MRI system. The portable MRI system has a lightweight magnet (e.g., less than 6.3 kg) and dimensions that allow it to easily be moved through doors and into tight spaces. In an embodiment, the portable MRI system is also low cost, for example, by using magnet materials that only cost on the scale of hundreds of dollars. The portable MRI system is configured to provide high depth resolution (e.g., 0.1 mm) MRI of tissues such as meninges, dermis, etc. In an embodiment, imaging of the tissues is to a depth of 3 cm. The portable single-sided MRI system is low-field and may be used to perform three-dimensional (3D) imaging. The disclosed portable, point-of-care MRI system may increase the utility of MRI by extending its reach and enabling application such as continuous bedside monitoring of a patient, MRI in Intensive Care Units (ICU) where patients cannot be transported into a magnet or even out of a hospital bed, MRI in rural, mobile or developing world settings where cost and siting prohibit the use of conventional systems, and MRI for routine screening and diagnosis where currently such applications are cost prohibitive.

Figure 1:
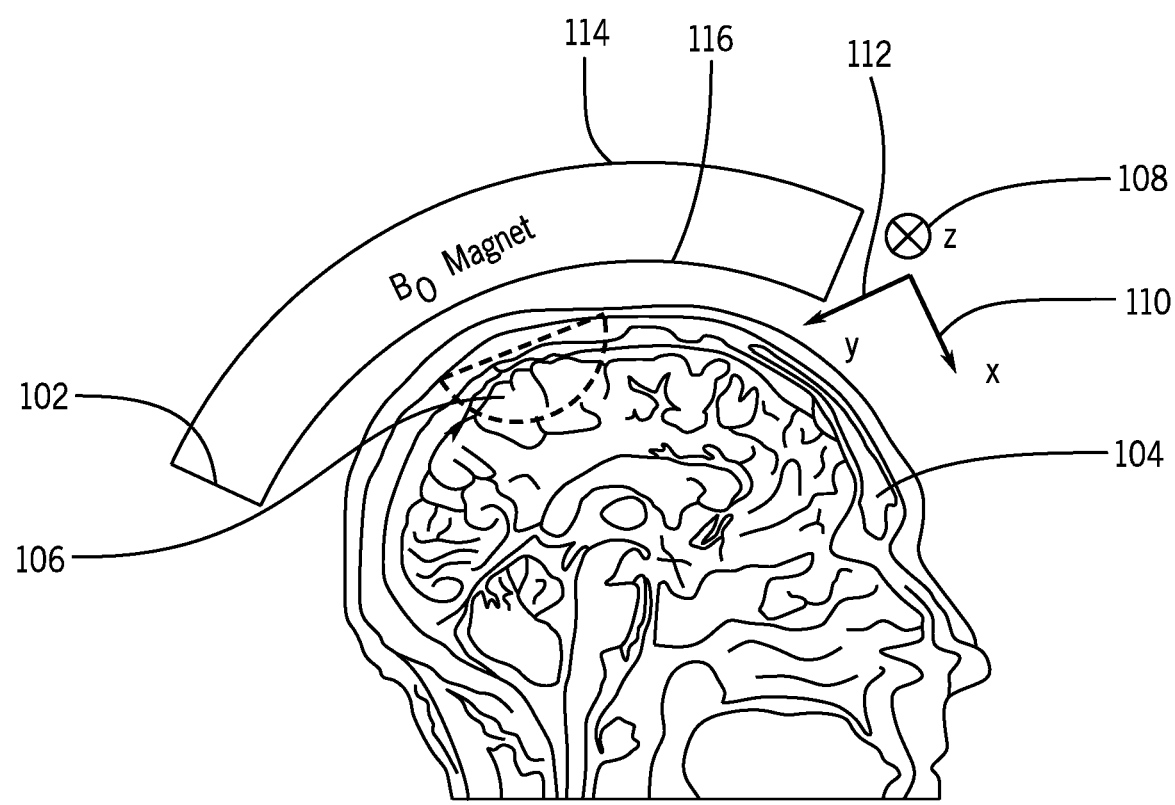
FIG. 1 is a schematic diagram showing a magnet for a portable MRI system, a region of interest and a $B_0$ axis in accordance with an embodiment.

In one embodiment, the portable, single-sided MRI system is configured for reduced field-of view brain imaging and capable of high resolution one-dimensional (1D), for example, depth profiling, to three-dimensional (3D) imaging. The MRI system includes a lightweight single-sided permanent magnet. FIG. 1 is a schematic diagram showing a magnet for a portable MRI system, a region of interest and a $B_0$ axis in accordance with an embodiment. In FIG. 1, a single-side magnet 102 (a $B_0$ magnet) has an outer curved surface 114 and an inner curved surface 116 and an overall cap-shape (e.g., the magnet 102 may have a form factor of a standard bicycle helmet). The cap-shape allows that magnet 102 to be positioned on top of an adult subject's head 104. In an embodiment, the magnet 102 is designed to closely fit an adult head 104 in order to maximize the $B_0$ field strength. As discussed further below, the magnet 102 is designed from a plurality of rare-earth (NdFeB) permanent magnet blocks arranged in a cap-shaped configuration on a cap-shaped former. Magnet 102 has a transverse-oriented $B_0$ field 108 with an imaging region of interest (ROI) 106 that includes part of the subject's skull and superficial cortex. In the embodiment of FIG. 1, the ROI 106 is hemi-ellipsoidal. Also shown in FIG. 1 for reference are an x-axis 110 and a y-axis 112. In an embodiment, the sensitive volume of the magnet 102 may extend 3 cm beneath the scalp (or epidural surface) and into the cerebral cortex when positioned on an adult head 104. An MRI system utilizing magnet 102 may be used for brain imaging over a 3D volume and may include gradient coils (not shown) placed external to the magnet 102 on the outer surface 114 and an RF coil (not shown) positioned on the inner surface of the magnet 102. In an embodiment, the curved surface of the ROI 106 may be chosen to match the RF coils $B_1$ sensitivity profile.

Figure 2:
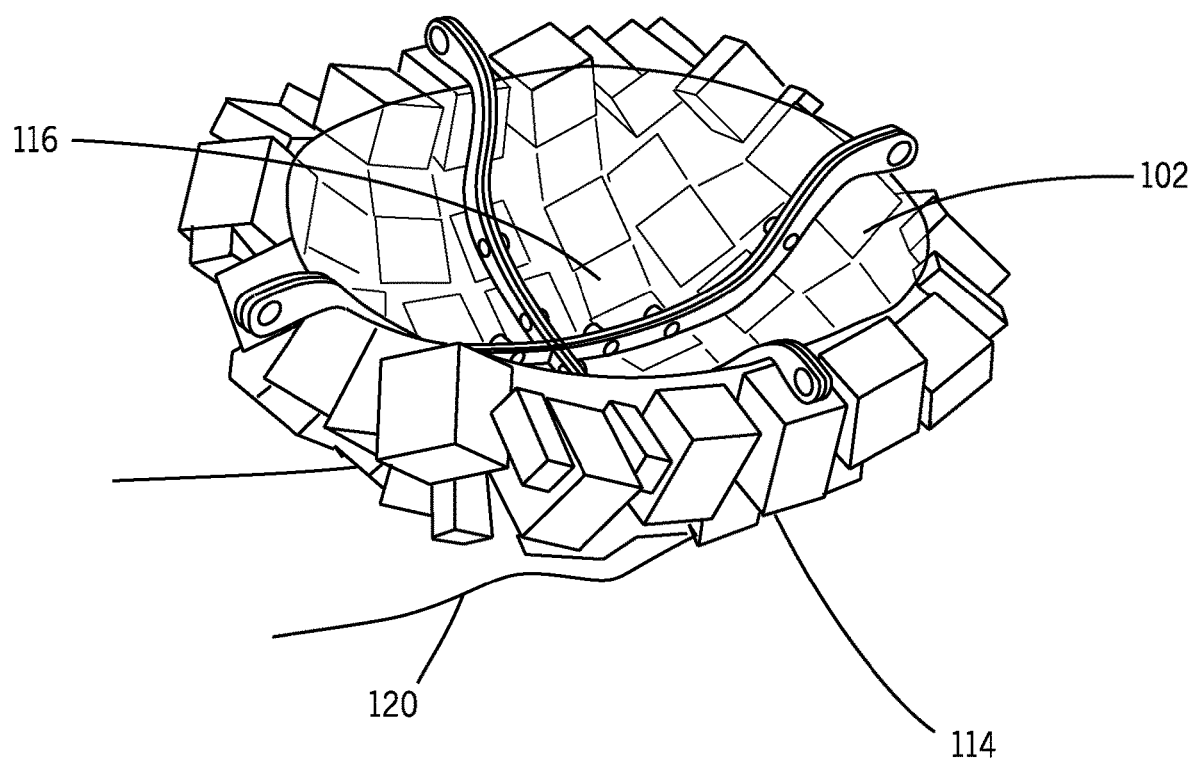
FIG. 2 is a diagram of a portable magnet in accordance with an embodiment.
Figure 3:
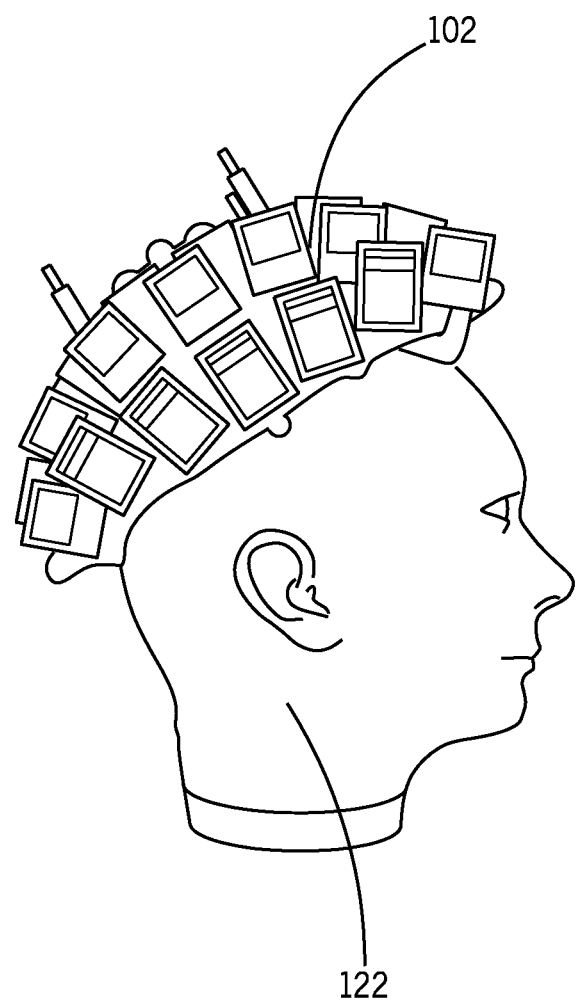
FIG. 3 is a diagram of a portable magnet and a subject showing placement of the magnet relative to a subject in accordance with an embodiment.

FIG. 2 is a diagram of a portable magnet in accordance with an embodiment and FIG. 3 is a diagram of a portable magnet and a subject showing placement of the magnet relative to a subject in accordance with an embodiment. In an embodiment, the portable magnet 102 may have dimensions so that is may be held by hand 120. As mentioned the concave inner surface 116 is designed to fit on a subject's head as shown in FIG. 3. FIG. 3 illustrates the magnet 102 placed on a subject's head 122.

Figure 4:
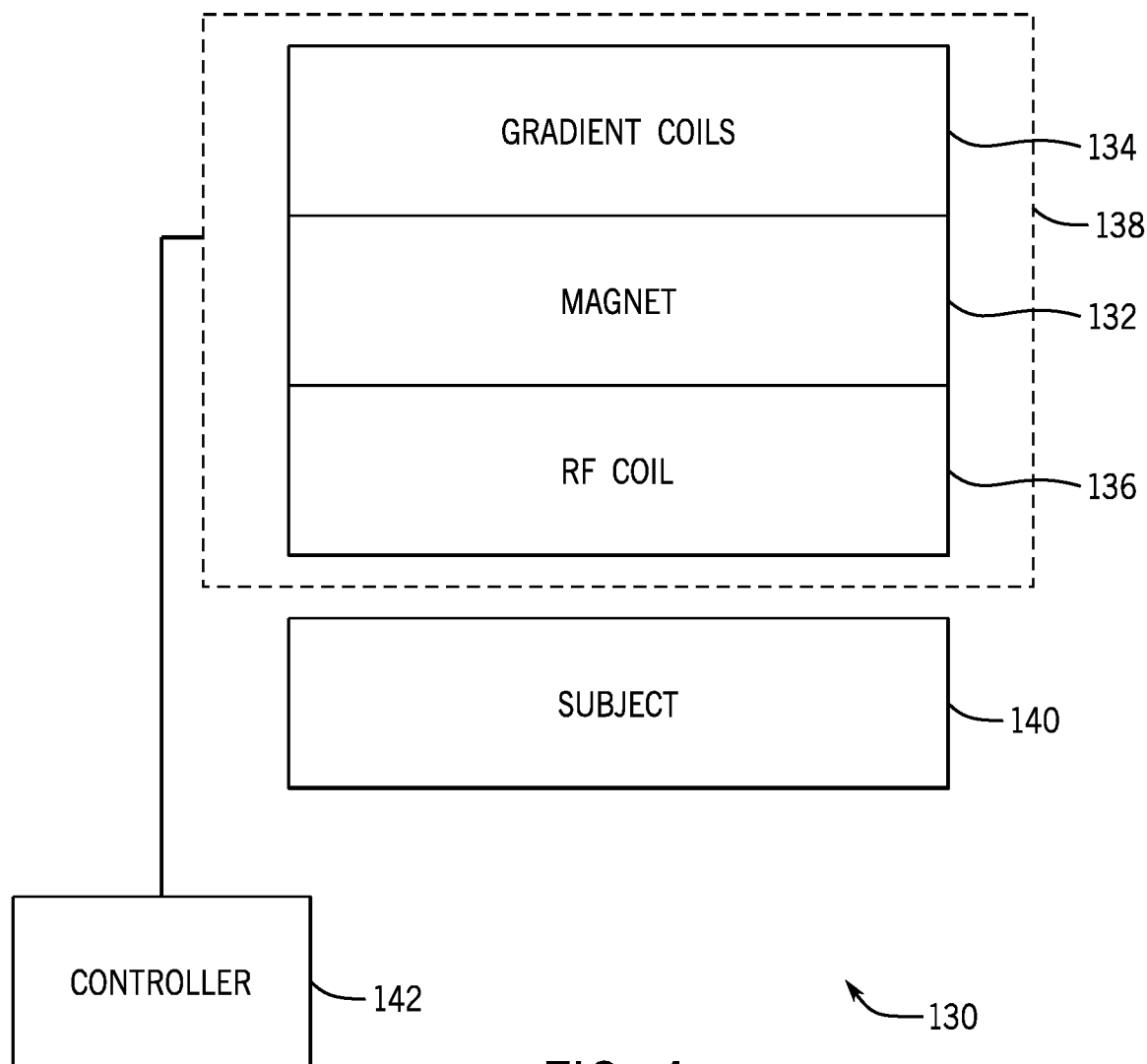
FIG. 4 is a schematic block diagram of a portable magnetic resonance imaging (MRI) system in accordance with an embodiment.

As mentioned, the portable MRI magnet 102 may be used in an MRI system configured for reduced field-of view brain imaging. FIG. 4 is a schematic block diagram of a portable magnetic resonance imaging (MRI) system in accordance with an embodiment. In FIG. 4, a schematic representation of the position of various elements in the MRI system with respect to one another is shown using blocks rather than the specific cap-shape described above. MRI system 130 includes a magnet assembly having a magnet 132, gradient coils 134, and RF coil 136 disposed within a housing 138 and positioned in close proximity to or on (e.g., close fitting) a subject 140. Magnet 132 is a single-sided magnet designed from a plurality of NdFeB permanent magnet blocks arranged in a cap-shaped configuration on a cap-shaped former. Single-sided magnets typically have large field gradients moving away from the magnet surface. This built-in $B_0$ gradient may be used for readout and slice select encoding. The magnet 132 may also be designed to avoid very strong (>1 T/m) gradients. Gradient coils 134 are configured to be positioned on the outer surface (e.g., surface 114 shown in FIG. 1) of the magnet 132. For example, a pair of gradient coils may be used to enable phase encoding on the other two directions. RF coil 136 is configured to be positioned on an inner surface (e.g., surface 116 shown in FIG. 1) of the magnet 132. RF coil 136 may be used to provide excitation and RF signal detection. As discussed further below, the assembly of the magnet 132, gradient coils 134 and RF coil 136 each include a former (not shown) on which the permanent magnet blocks, gradient coils, and RF coil are mounted.

Figure 5:
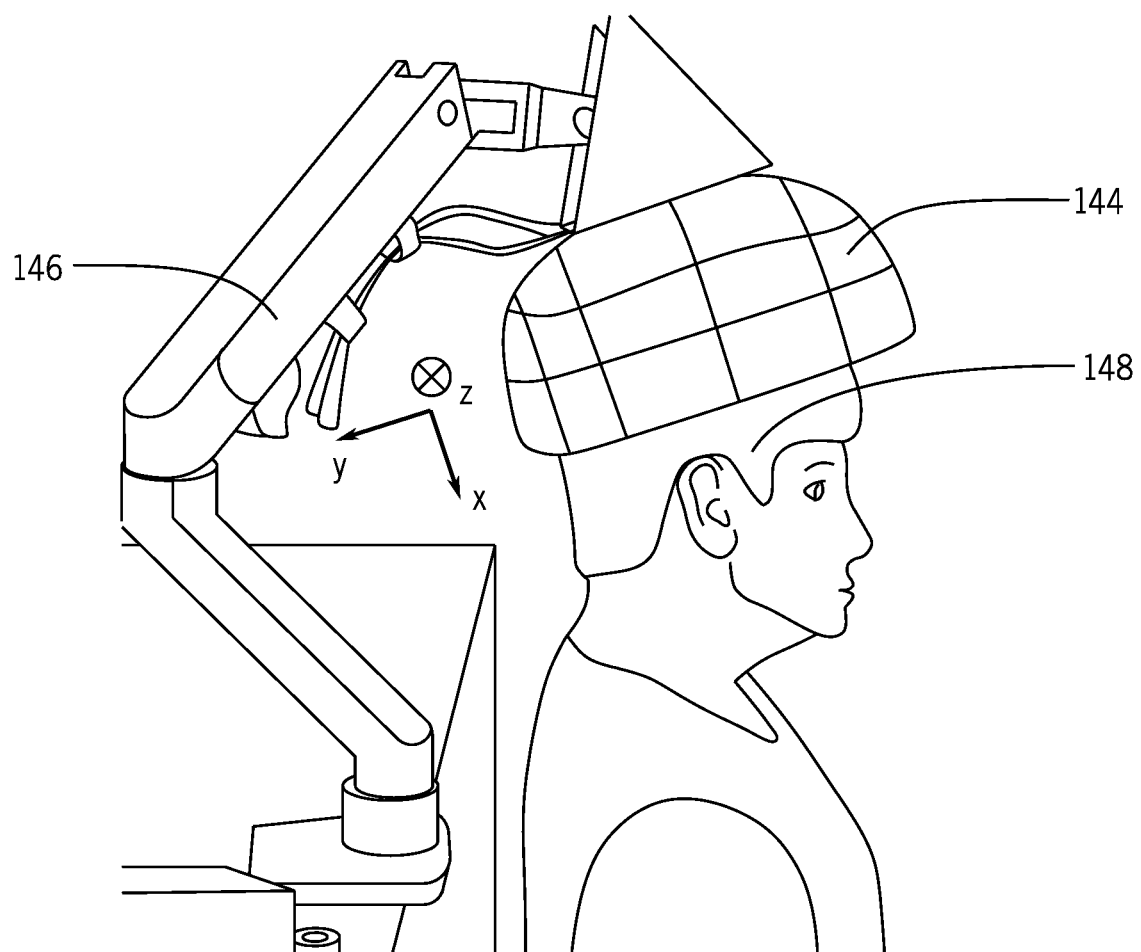
FIG. 5 is a schematic diagram of a portable MRI system and an articulated arm in accordance with an embodiment.

A controller 142 is coupled to the magnet 132, gradient coils 134 and RF coil 136 and configured to control the operation of the magnet 132, gradient coils 134 and RF coil 136 to acquire MR images of the subject 140. For example, controller 142 is configured to drive the gradient coils 134 and RF coil 136 for gradient waveform generation and RF waveform generation, respectively, using known hardware and methods. In addition, controller 142 is configured to record MR signals received by the RF coil 136 from the subject 140. Controller 142 may also be configured to generate images based on the received MR signals using known reconstruction methods. In an embodiment, the housing 138 with the magnet 132, gradient coils 134 and RF coil 136 may be attached to an articulated arm as shown in FIG. 5. FIG. 5 is a schematic diagram of a portable MRI system and an articulated arm in accordance with an embodiment. In FIG. 5, a magnet assembly 144 is attached to an articulated arm 146 which allows the magnet assembly 144 to be positioned and moved about a subjects head 148. Using the articulated arm 146, the magnet assembly 144 may be arbitrarily positioned allowing movement of the sensitive volume of the single-sided magnet to different regions of the brain. This embodiment may allow the magnet assembly 144 to be, for example, positioned on the head of a bed-bound subject or to be placed on a subject for an extended time for continuous monitoring applications.

Figure 6:
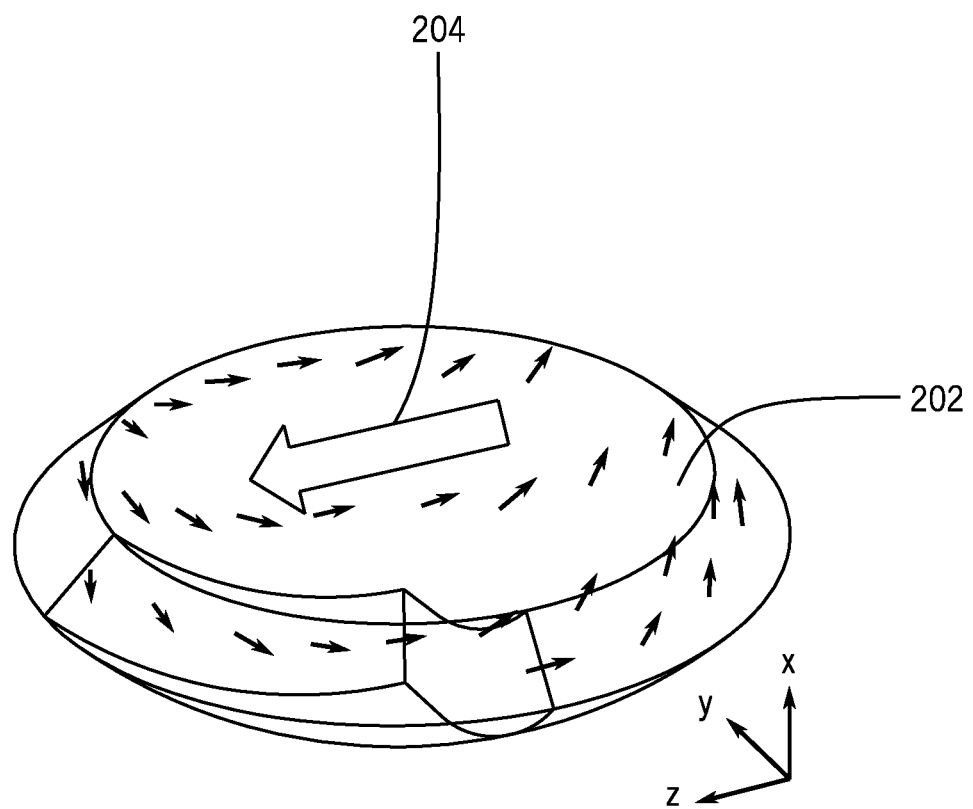
FIG. 6 shows an example cap-shaped section of a Halbach sphere for optimization of magnet design in accordance with an embodiment.
Figure 7:
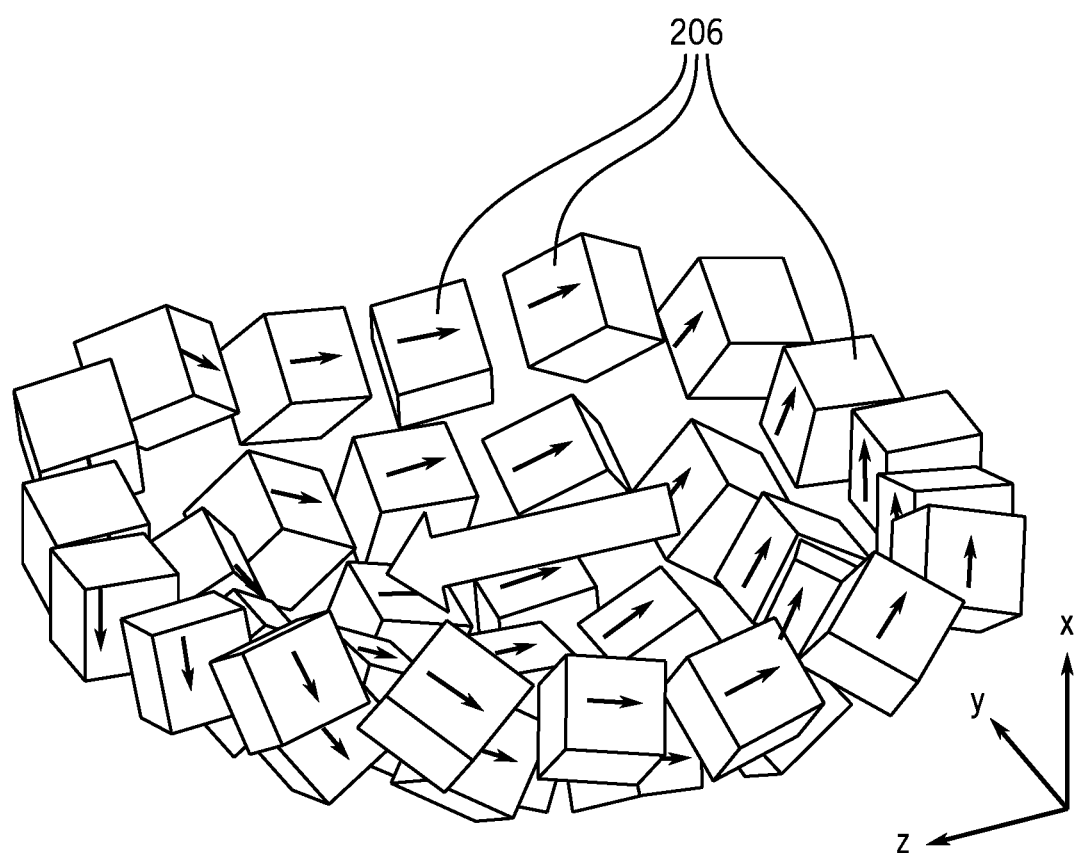
FIG. 7 shows an example discretized Halbach sphere section in accordance with an embodiment.

As mentioned above, the portable, single-sided magnet 102 (shown in FIG. 1) is designed from a plurality of NdFeB permanent magnet blocks arranged in a cap-shaped configuration on a cap-shaped former and may be used to obtain images of a cortical region of a subject that it is positioned over. In an embodiment, the arrangement of the plurality of rare-earth permanent magnet blocks is optimized for the cap-shaped configuration. For example, the magnet may be designed with a genetic algorithm optimizing homogeneity over a field-of-view (FOV) and the built-in gradient for slice-selection or readout encoding. For example, the placement of the NdFeB material may be chosen using the genetic optimization framework. In an embodiment, the optimization process starts with an equatorial portion (or "cap-shaped" section) or of an ideal Halbach sphere. FIG. 6 shows an example cap-shaped section of a Halbach sphere for optimization of magnet design in accordance with an embodiment. The continuous magnet material section 202 of a Halbach sphere magnet approximates the desired magnet shape (i.e., cap-shaped) and $B_0$ 204 direction. The continuous magnetization pattern was then discretized into a plurality of blocks as shown in FIG. 7. In FIG. 7, the discretized Halbach sphere section approximates the continuous magnetization pattern as an assembly of magnet blocks 206. In an embodiment, the continuous magnetization is discretized into 37 magnet blocks 206. The discretized Halbach sphere section is practical to construct and has the desired field orientation, but is not optimized for in-plane homogeneity or gradient strength. In an embodiment, the optimization may be performed by allowing the genetic algorithm to alter the sizes, block magnetization grade, compositions, and translational position of each magnet block 206.

Figure 8:
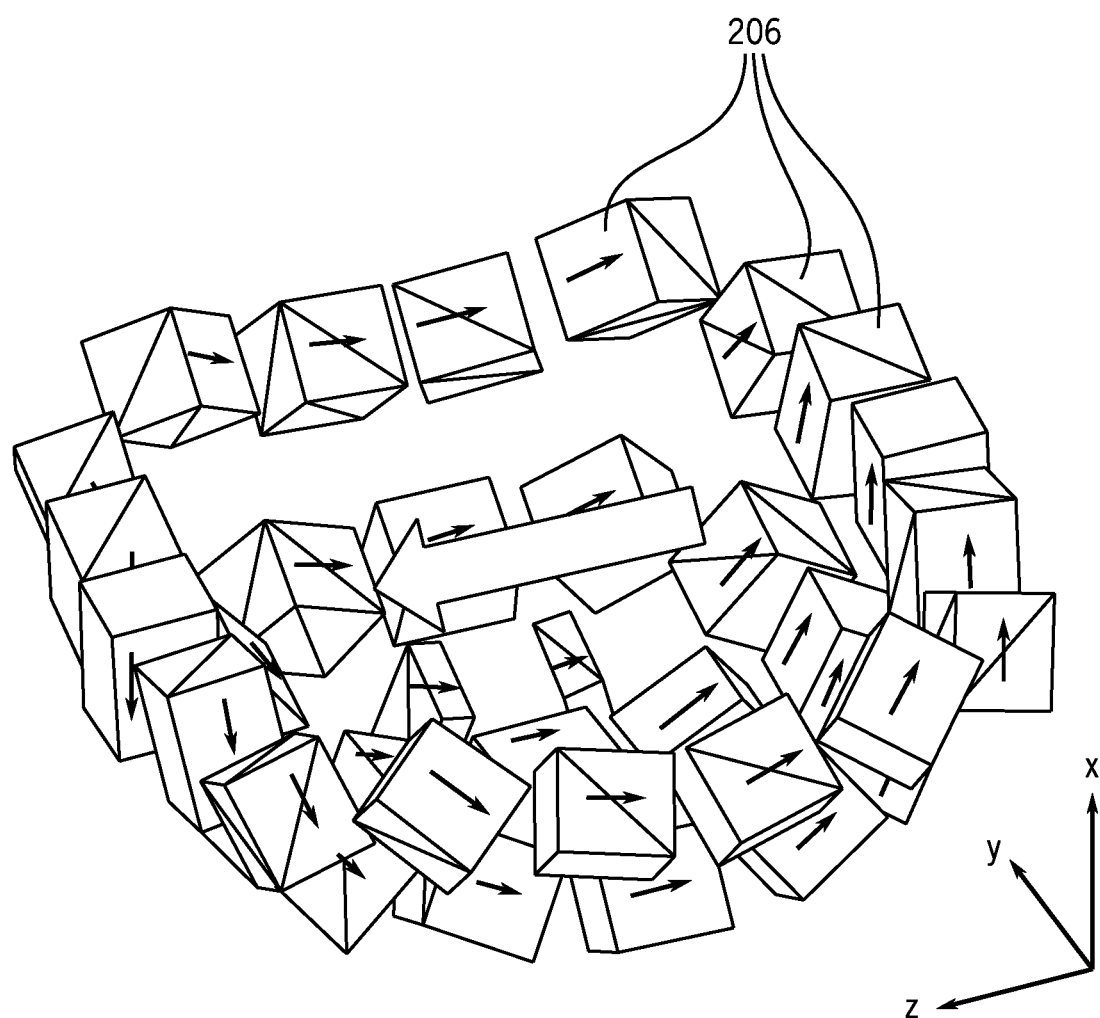
FIG. 8 shows an example optimized discrete block magnet design in accordance with an embodiment.

FIG. 8 shows an example optimized discrete block magnet design in accordance with an embodiment. In an example optimization for a discretized magnetization with 37 blocks, the positions of the simulated blocks 206 were allowed to vary along the x axis by up to +/−1 cm and 6 of the 37 blocks were allowed to move along the z axis by up to +/−1 cm during optimization. In this example, the composition of each block 206 may take one of seven size/material combinations ranging from a non-magnetic block to an N52-grade block of dimensions 25.4 mm×25.4 mm×34.9 mm. The cost function used was the % range of $B_0$ across a 3D grid of uniformly-spaced set of points within the target ROI (e.g., 100×$\Delta B_0/B_0$). This cost function determines the bandwidth (BW) of the signal and has implications for the Q of the RF coils needed to excite and detect spins across the ROI. A hemi-ellipsoidal ROI with 4 cm major radii and a 3 cm minor radius was used. As mentioned above with respect to FIG. 1, this ROI is designed to penetrate 3 cm into the cerebral cortex and roughly matches the excitation region of the RF coil (e.g., a loop transmission RF coil). Additionally, in this example the minimum $B_0$ was constrained to be >50 mT. Prior to optimization, the B-field maps for each of the seven block types were calculated. Appropriately shifting each block's field map based on the block position and superimposing the field enabled rapid computation of the magnet assembly's B-field map during optimization. In this example, the $B_0$ field map for the final design was simulated to verify the result. FIG. 8 shoes the result of the example optimization.

Figure 9:
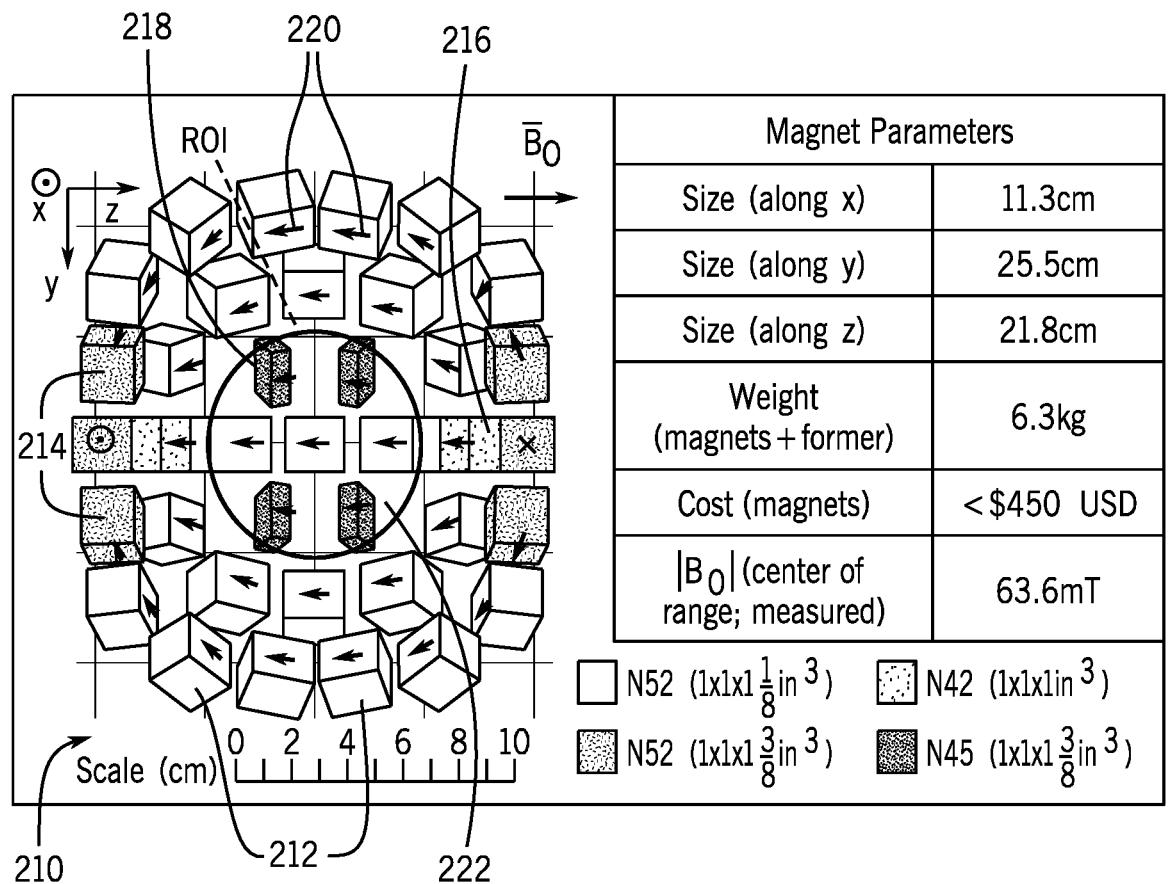
FIG. 9 shows an example optimized magnet assembly in accordance with an embodiment.
Figure 10:
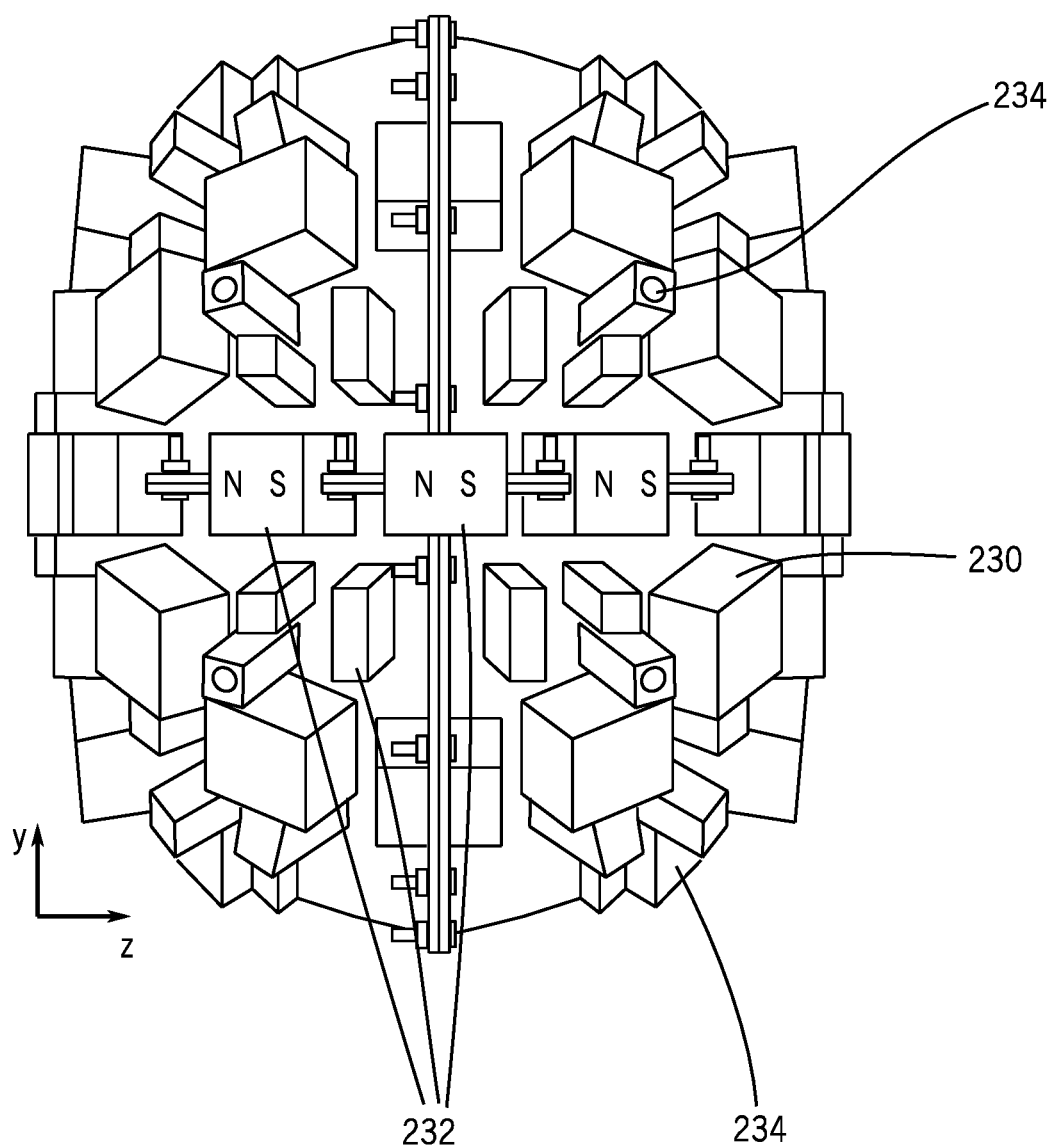
FIG. 10 shows an example magnet former with slots in accordance with an embodiment.
Figure 11:
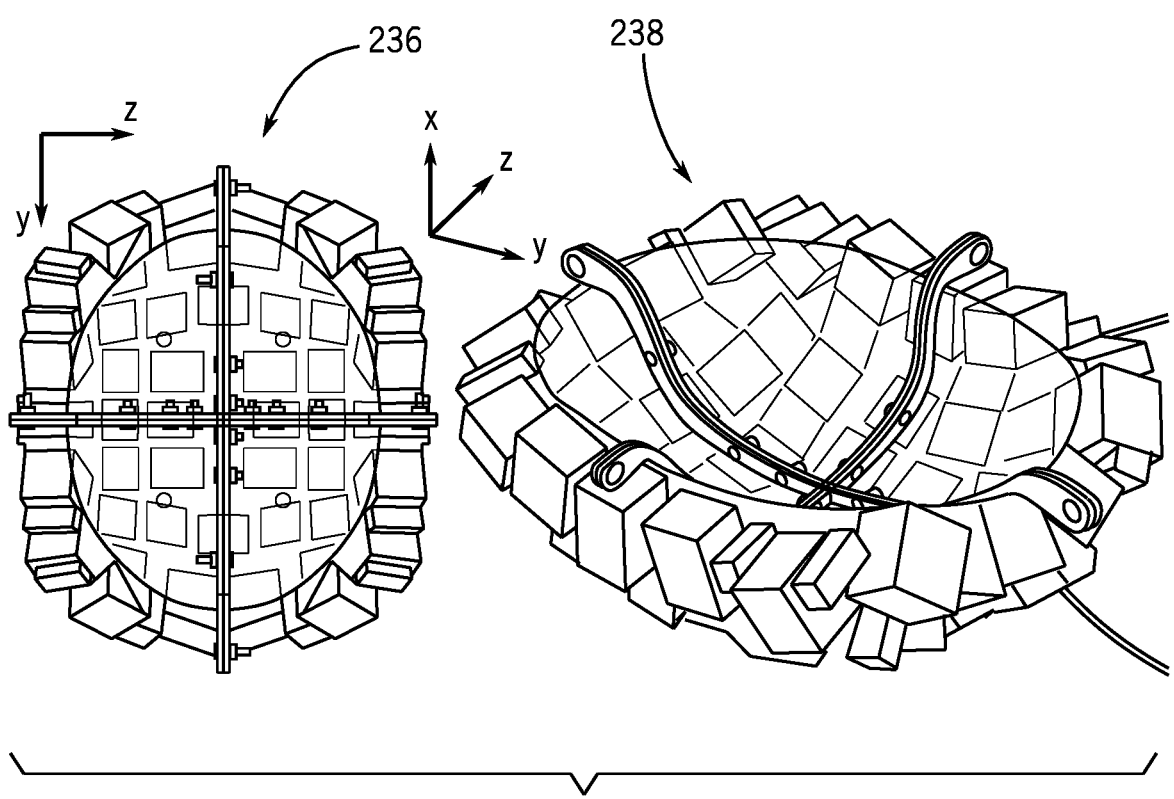
FIG. 11 shows an YZ-plane view and an oblique view of a final assembled magnet in accordance with an embodiment.

The optimal magnet design (e.g., the example optimized design shown in FIG. 8), may then be converted into a physically-realizable assembly of NdFeB permanent magnet blocks. FIG. 9 shows an example optimized magnet assembly in accordance with an embodiment. The example optimized magnet assembly 210 is shown as an assembly of standard size and standard material NdFeB blocks 212, 214, 216 and 218. The magnet assembly includes magnet blocks of various size and material combinations including N52 blocks 212 of size 1×1×1⅛ in$^3$, N52 blocks 214 of size 1×1×1⅜ in$^3$, N42 blocks 216 of size 1×1×1 in$^3$, and N45 blocks 218 of size 1×1×⅜ in$^3$. In an embodiment, some blocks may be constructed by sticking multiple smaller blocks together (e.g., an N52 1"×1"×1⅛" block contained an N52 1"×1"×1" block and an N52 1"×1"×⅛" bock). The example optimized magnet assembly 210 had overall dimensions of 11.3 cm×22.5 cm×21.8 cm and weighed 6.3 kg. The arrows 220 indicate the direction of magnetization. FIG. 9 also shows an optimized ROI 222. A former is used to hold the magnet blocks prescribed by the optimized design. FIG. 10 shows an example magnet former with slots in accordance with an embodiment. The magnet former 230 may be constructed of a material such as acrylic. In an embodiment, the magnet former 230 is constructed using 3D printing. The magnet former 230 includes a plurality of slots 234. The final assembled magnet blocks 232 are inserted into the slots 234 of the magnet former and may be secured to the former 230 using, for example and epoxy. FIG. 11 shows an YZ-plane view 236 and an oblique view 238 of a final assembled magnet in accordance with an embodiment.

As mentioned, the portable magnet assembly may include a pair of gradient coils (e.g., gradient coils 134 shown in FIG. 4). In an embodiment, two cap-shaped gradient coils are provided that are configured for blipped phase encoding of a spin-echo train along the y- and z-axes. The gradient coils are constructed on a gradient coil former that may be positioned on an outer surface of the magnet. This design saves valuable space within the magnet to enable a stronger $B_0$ and allows for improved gradient linearity, at the cost of reduced gradient efficiency. In addition, weak unshielded gradient coils do not produce significant eddy current effects if placed either inside or outside an NdFeB magnet. In an embodiment, the gradient winding patterns for the $G_y$ and $G_z$ gradient coils are designed using a modified Boundary Element Method (BEM) Stream Function with L1-regularization. The target fields for the $G_y$ and $G_z$ coils included both the desired linear terms (Y and Z, respectively) and an additional 2nd-order term (XY and XZ, respectively). The efficiency of a single-sided gradient coil decreases as one moves away from it (in this case, along x), and this decrease is manifested as undesired XY and XZ terms for the $G_y$ and $G_z$ coils, respectively. The addition of the 2nd-order terms in the target field of the BEM Stream Function design helps compensate for the spurious XY and XZ terms improving linearity over the target ROI.

Figure 12:
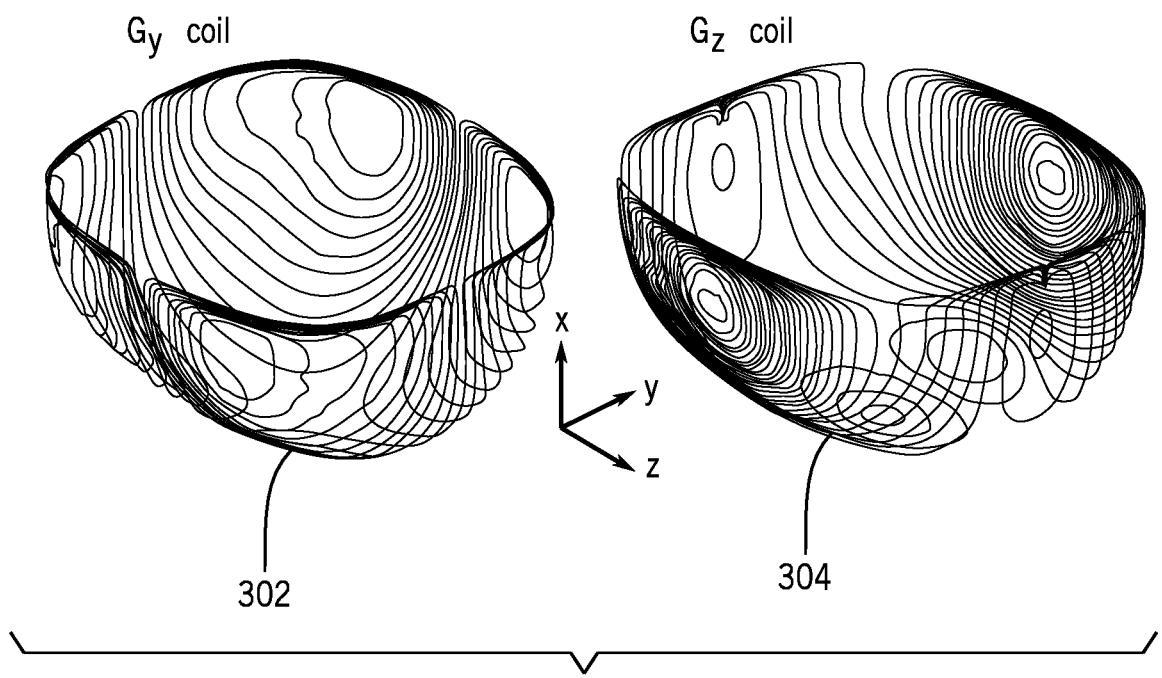
FIG. 12 shows an example $G_y$ gradient coil design and an example $G_z$ gradient coil design in accordance with an embodiment.
Figure 13:
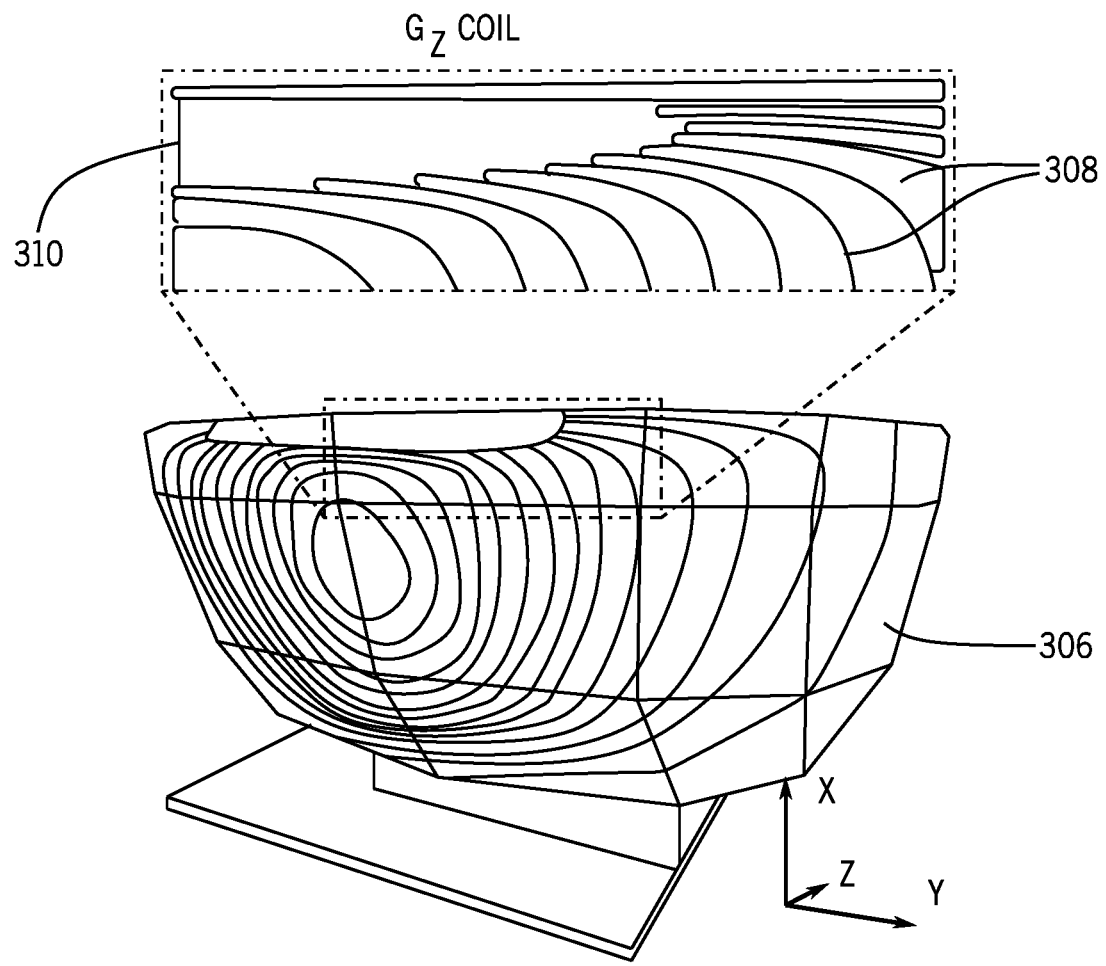
FIG. 13 shows an example gradient coil former with wire grooves in accordance with an embodiment.
Figure 14:
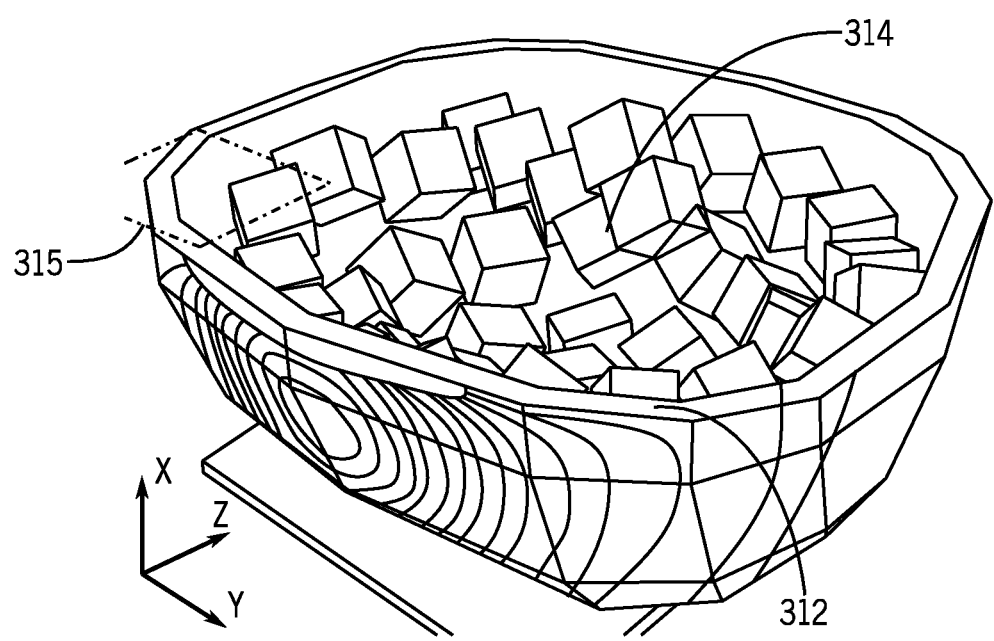
FIG. 14 shows an example gradient coil and magnet assembly in accordance with an embodiment.
Figure 15:
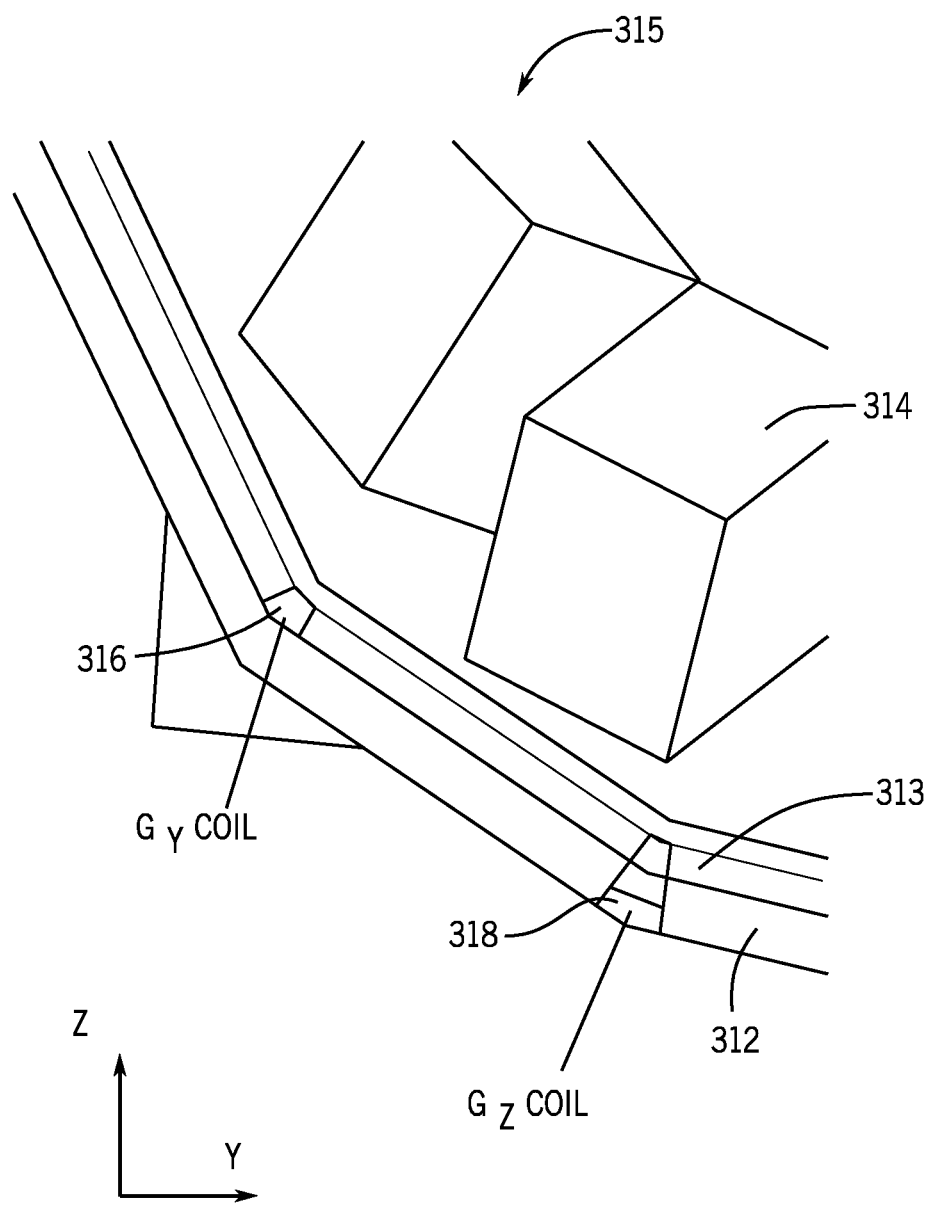
FIG. 15 shows an expanded detail view of a portion of the gradient coil and magnet assembly of FIG. 14 in accordance with an embodiment.

The optimized stream functions were converted into wire winding paths as shown in FIG. 12 which shows the numerical designs for a $G_y$ 302 gradient coil and a $G_z$ 304 gradient coil. To construct the gradient coils, the optimized stream functions (winding paths) 302 and 304 were then projected onto a piecewise-linear surface of a gradient coil former as shown in FIG. 13. FIG. 13 shows an example gradient coil former with wire grooves in accordance with an embodiment. In an embodiment, a gradient coil former 306 may be constructed by 3D printing a polycarbonate helmet former (e.g., ~2 mm thick). A series of triangular and rectangular facets may then be epoxied onto the outside surface of this basic helmet structure of the former. The triangular and rectangular pieces contain wire grooves 308 as shown in the exploded view of the $G_z$ gradient coil 310. The wire grooves correspond to the numerical winding paths 302 and 304 (shown in FIG. 12). The wire grooves 308 are configured to receive magnet wire, for example, the wire grooves 308 may be configured for press-fitting two layers of magnet wire into the polycarbonate former. In an embodiment, after winding the $G_y$ coil, an additional layer of triangular and rectangular grooved pieces may be epoxied external to the $G_y$ coil to form the $G_z$ coil. FIG. 14 shows an example gradient coil and magnet assembly in accordance with an embodiment and FIG. 15 shows an expanded detail view of a portion of the gradient coil and magnet assembly of FIG. 14 in accordance with an embodiment. In FIG. 14, the completed $G_y$ and $G_z$ gradient coils and former assembly 312 is shown positioned around a magnet 314. The expanded detail view 315 in FIG. 15 shows the $G_y$ coil 316 and $G_z$ coil 318 on a gradient coil former 312. The gradient coil former 313 and gradient coils 316, 318 assembly 312 is positioned around the magnet 314.

Figure 16:
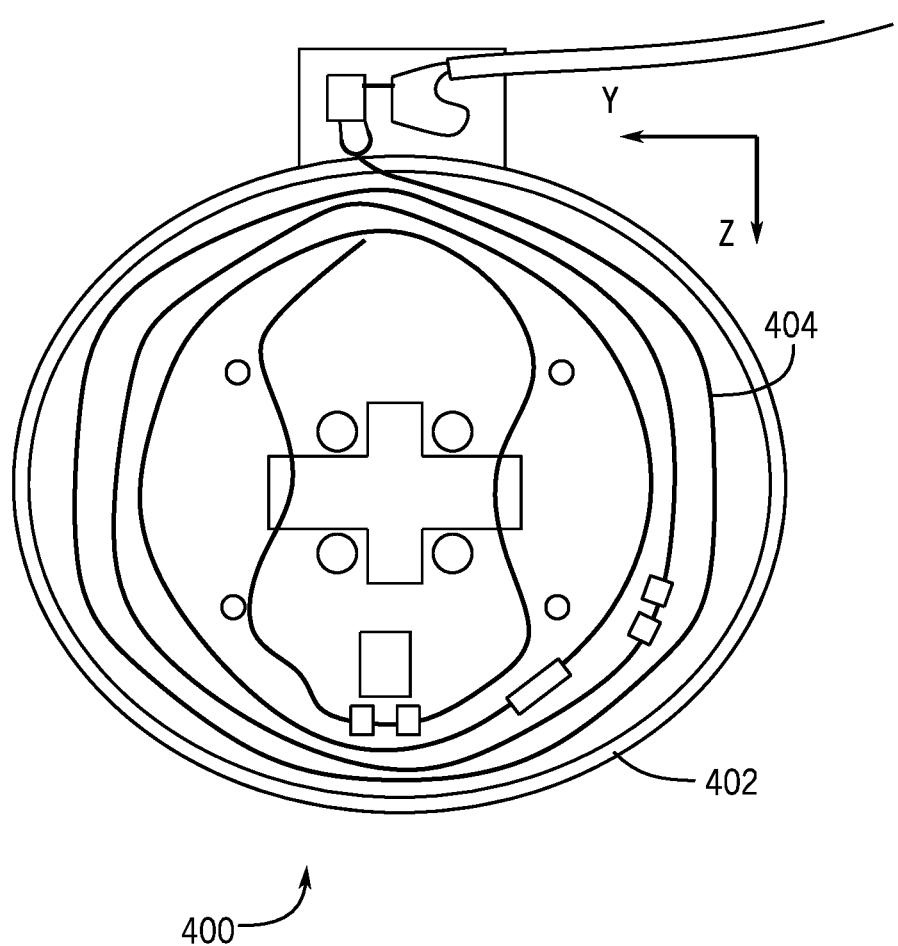
FIG. 16 shows an example RF coil assembly in accordance with an embodiment.

As mentioned, the portable magnet assembly may also include an RF coil (e.g., RF coil 136 shown in FIG. 4). FIG. 16 shows an example RF coil assembly in accordance with an embodiment. In FIG. 16, an RF coil 400 assembly may be constructed by designing an RF coil (or winding) on a surface (or RF coil former) 402 configured to fit inside the $B_0$ magnet. In an embodiment, the RF coil may be designed using the same BEM stream function approach described above with respect to the gradient coils. The same static-field approach used for the gradient design may be used because the RF coil dimension (~0.1 m) was much less than the wavelength at the Larmor frequency (f~2.67 MHz; lamda~112 m). An RF coil winding may be designed to optimize spatial $B_1$ uniformity within the target ROI (e.g., ROI 106 shown in FIG. 1). The RF coil 400 may be constructed by press-fitting wire 404 (e.g., 4 turns of Litz wire; OD=0.1 mm). In an embodiment, a 1-Ohm resistor may be placed in series with the coil 404 to increase the 3 dB bandwidth to 157 kHz (BW without resistor=72 kHz).

In an embodiment, the described portable, lightweight (e.g., <6.3 kg including the former) $B_0$ magnet was designed to achieve a 64 mT average field over the imaging region (e.g., ROI 106 shown in FIG. 1) and a built-in field gradient of ~117 mT/m (~5000 Hz/mm) at a material cost on the scale of several hundreds of dollars. In an embodiment, the ROI may be a ~3×8×8 cm³ volume. In an embodiment, the MRI system including the $B_0$ magnet, gradient coils and RF coil may be designed to be a weight of less than 10 kg, e.g., 8.3 kg. In an embodiment, the $G_y$ gradient coil was designed with an efficiency of 1.117 mT/m/A at the ROI center and linearity of 33.3% (along the y-axis) and the $G_z$ gradient coil was designed with a mean efficiency of 1.019 mT/m/A at the ROI center and a linearity of 27.8% (along the z-axis). In this embodiment, the inductance of gradient coils were: 273.3 uH ($G_y$) and 178 uH ($G_z$) and the $G_y$ and $G_z$ gradient coil DC resistances were 1.15Ω and 1.01Ω, respectively.

The MRI system described herein may be used as a point-of-care system to acquire 1D and 3D images, for example of the brain, over a reduced FOV sensitive region. In an embodiment, a shimming capability may be applied to the $B_0$ magnet or the optimization may more explicitly penalize peak ("min-max") inhomogeneities to mitigate any reduction of the slice thickness or signal level. In another embodiment, the center three points of each spin echo may be averaged together during the image reconstruction to introduce a dependence on local $T_2^*$. In yet another embodiment, an image normalization procedure may be used during image reconstruction to address hyperintense regions in certain slices of a 3D acquisition. In another embodiment, gradient non-linearity effects may be mitigated by refining the gradient coil design or compensated for in the pulse sequence by adjusting the encoded FOV for each slice. Other options include post-processing approaches which apply a gradient nonlinearity correction or generalized image reconstruction approach.

In an embodiment, control of the built-in $B_0$ gradient is used to provide equal amounts of signal per bandwidth at different positions in the ROI. An improved magnet design with higher linearity (but limited gradient strength) may be used to mitigate artifacts. Additionally, an RF coil with increased spatial uniformity and coverage may improve images. In an embodiment, this may be achieved by either a physically larger RF coil or an RF coil with more windings. Adding winding of increasing size boosts the inductance of the coil more quickly than the resistance. However, this in turn would increase the Q of the coil and decrease its bandwidth, exacerbating any coil BW issue. Resolving issues stemming from narrow coil bandwidth may be approached by shaping the spectral resonance response of the coil. On approach for creating an RF coil with a more uniform frequency response is using a series resistor as described above with response to FIG. 16. Several approaches for creating a coil with a more uniform frequency response without a series resistor include quasi-transmission line coils, coupled resonant structures, used of a low-impedance preamplifier, and inductively coupled negative feedback mechanisms.

In an embodiment, image SNR may be improved either with improved system hardware or an improved acquisition. For example, either a stronger $B_0$ magnet or more uniform $B_0$ magnet (enabling reduced-bandwidth acquisitions) would improve SNR. A stronger $B_0$ magnet in the same form factor may be achievable by allowing for a higher density of magnetic material or by adding a second layer or otherwise increasing the thickness of the cap-shaped magnet. A more uniform magnet may be realized by the use of $B_0$ shim coils or shim material. An improved RF coil may also be used to increase SNR. In an embodiment, removing the 1-Ohm resistor in the coil and increasing the BW with more sophisticated, lossless approaches may be used to improve performance. Acquisition improvements may also be used increase image SNR. In an embodiment, weighting the sampling density to the center of k-space or utilizing sparsity priors such as compressed-sensing type acquisitions or denoising approaches may be used to boost SNR. In another embodiment, for an acquisition using a RARE pulse sequence a flipback pulse after each RARE train may assist with longitudinal $M_2$ recovery and increase available signal. The spin echoes in the 3D acquisition are temporally very narrow (due to field inhomogeneity), and the acquisition window length could be significantly shortened. This would free up sequence time for more echoes, allowing averaging down the echo train. Such an approach may be impractical at high field due to safety limits on the RF specific absorption rate (SAR), but at 64 mT the SAR for such an acquisition is negligible.

In an embodiment, the portable MRI system may also include shielding, for example, either a passive shielding approach such as draped conductive cloth, or an active interference cancellation system. In another embodiment, to address temperature induced drift in $B_0$ various approaches may be used including a feedback system controlling a heater to stabilize the temperature, use of a combination of rare-earth materials with differing temperature coefficients, or the use of a field probe to measure $B_0$ drift for incorporation into a model-based image reconstruction algorithm.

As mentioned the portable $B_0$ magnet MRI system may be used for reduced-FOV brain imaging. In an embodiment, the portable MRI system may be used for continuous monitoring (such as for hemorrhage) during postoperative care. In addition, the superior sagittal sinus (SSS) is often analyzed as a marker of cerebral vascular dynamics, including in MR studies. In another embodiment, as a large, superficial structure, the SSS could be imaged by the portable MRI system, potentially with the used of adiabatic inversion in the inhomogeneous magnetic field to perform spin-tagging for blood flow assessment. Traumatic brain injury (TBI) often results in a subdural hematoma (a large pool of blood forming adjacent to the dura). In another embodiment, the portable MRI system may be used to assess and monitor subdural hematoma, including, for example, at the accident site. The built-in $B_0$ gradient field (e.g., 117 mT/m) of the portable $B_0$ magnet may be larger than the gradient amplitude achievable on existing clinical scanners and may be used for providing diffusion-weighted image contrast to assess pathology such as ischemic stroke.

Figure 17A:
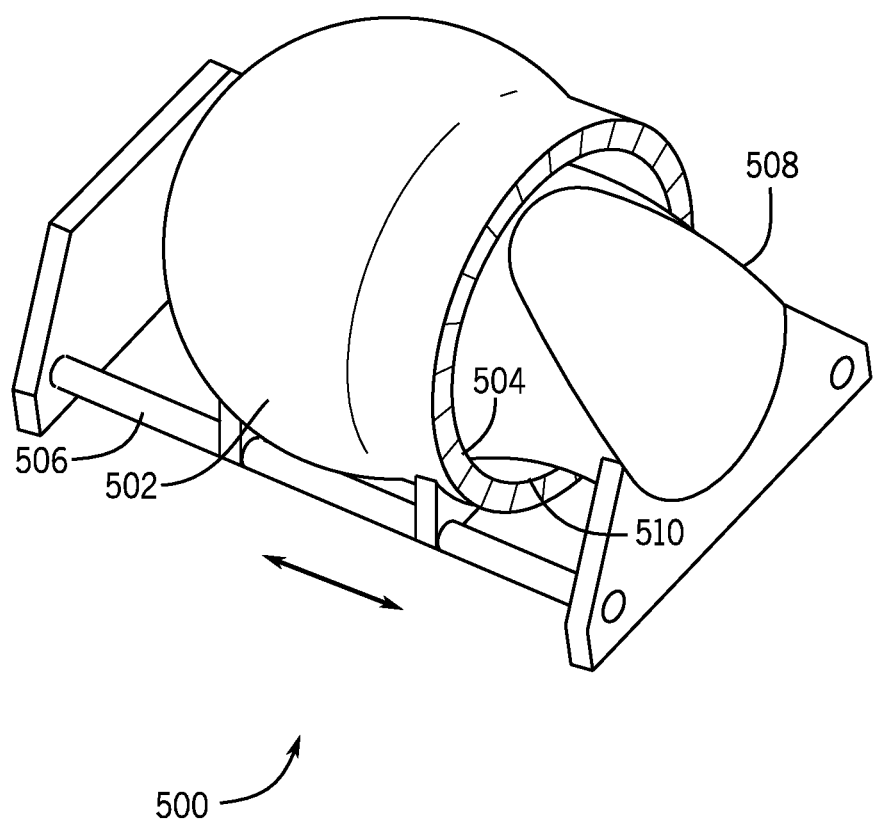
FIGS. 17a and 17b show an example whole-brain MRI system in accordance with an embodiment.
Figure 17B:
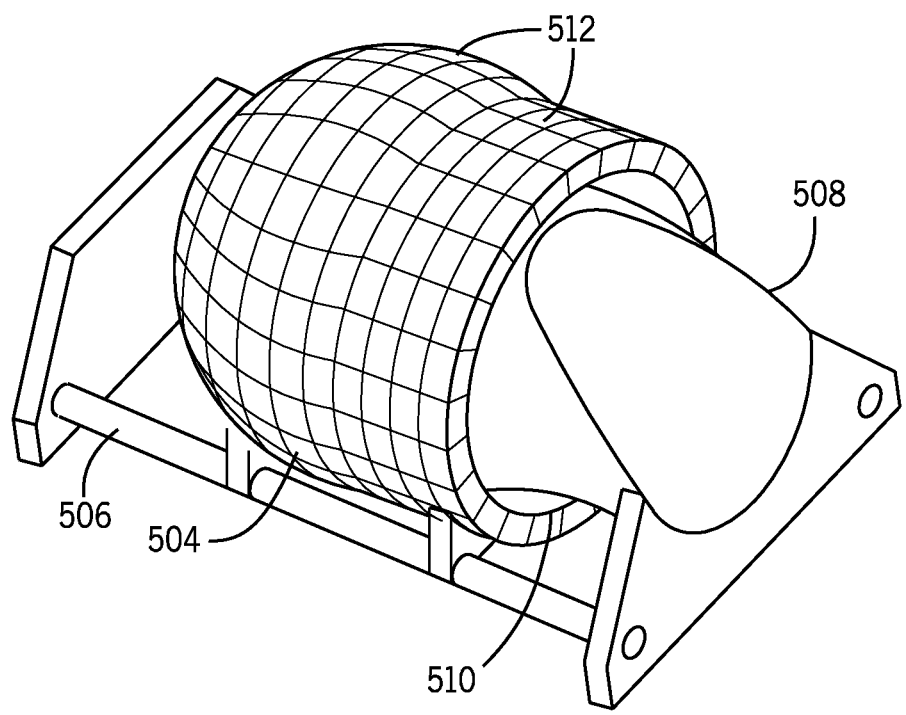

In another embodiment, a close-fitting, lightweight, whole-brain MRI system may be constructed with a whole-brain MRI magnet having a uniform $B_0$-field over a head-sized region of interest (ROI) for conventional gradient encoding. In an embodiment, the whole-brain magnet may have a $B_0$ of 86 mT and weigh under 25 kg. The whole-brain MRI magnet may be constructed of NdFeB blocks configured in a helmet-shape and to closely fit on the subject's head. The whole-brain MRI system includes the whole-head $B_0$ magnet, gradient coils positioned external to the $B_0$ magnet and an RF coil positioned inside the magnet. FIGS. 17a and 17b show an example whole-brain MRI system in accordance with an embodiment. FIG. 17a shows a whole-brain MRI system 500 including a magnet assembly consisting of gradient coils 502 positioned over a $B_0$ magnet which is positioned over an RF coil 510. The magnet assembly is positioned over a subject's head 508 and has a helmet-shape. In an embodiment, the magnet assembly may be mounted to a sliding assembly 506 to allow the placement and removal of the magnet assembly from over the subject's head 508. FIG. 17b shows the magnet 504 positioned over the RF coil 510 without the gradient coils 502. As discussed further below, magnet 504 may be constructed from a plurality of NdFeB permanent magnet blocks 512.

Figure 18:
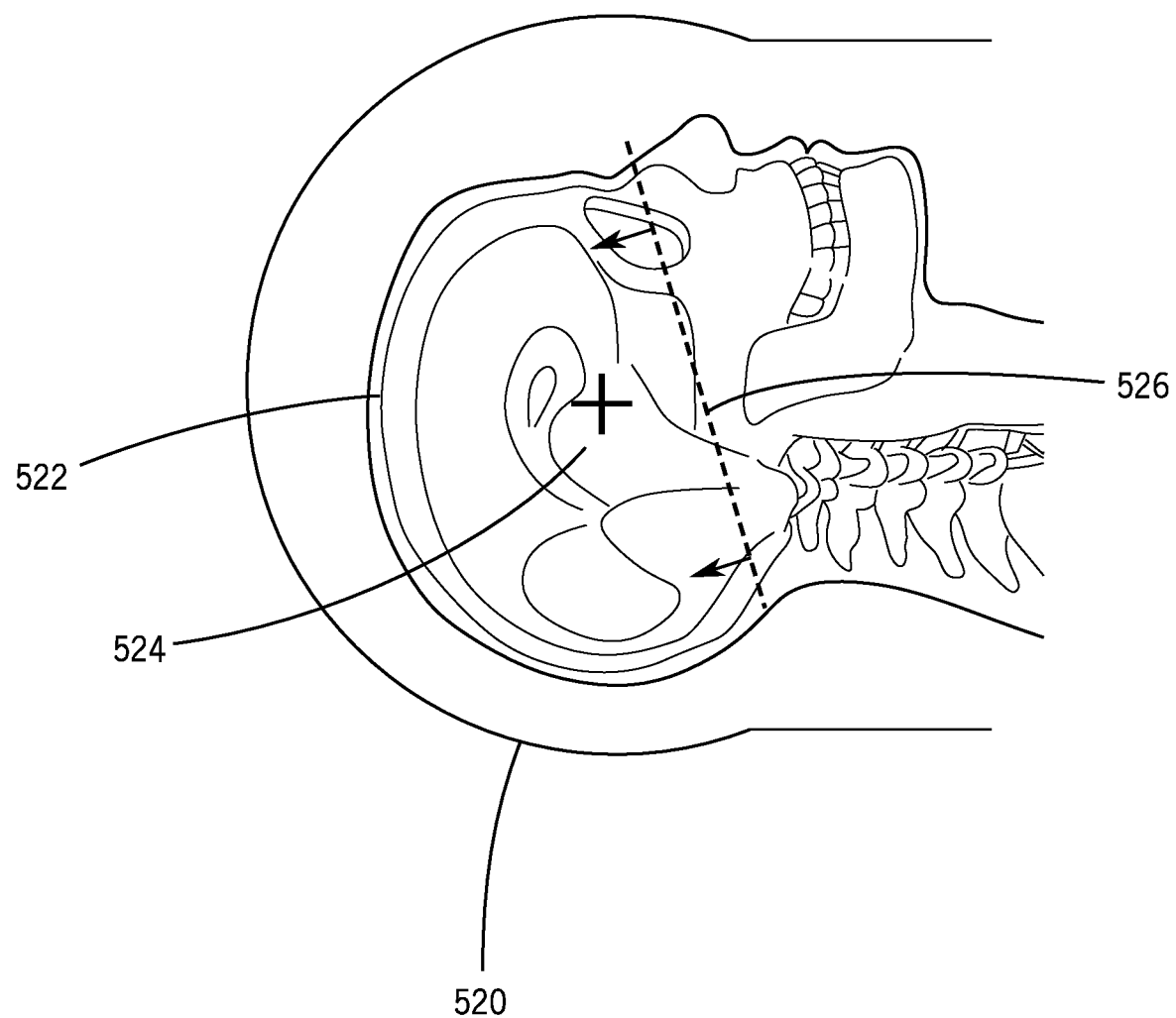
FIG. 18 shows a bulb-shaped surface surrounding a subject's head used in optimization of a portable whole-head magnet in accordance with an embodiment.

The $B_0$ magnet may be designed by optimizing the distribution of rare-earth magnets needed to maximize homogeneity over a brain-shaped ROI. In an embodiment, an interior point method may be used to optimize magnet block size (and thus magnetic dipole size) for a helmet-shaped Halbach geometry. FIG. 18 shows a bulb-shaped surface surrounding a subject's head used in optimization of a portable whole-head magnet in accordance with an embodiment. The three components of a magnetic dipole moment vector are optimized at 296 points on a bulb-shaped surface 520 that surrounds an adult head/neck 522 to design a helmet with 296 magnet blocks that minimizes the absolute range of $B_0$ magnitude over a head-shaped ROI 524. In this embodiment, the head-shaped ROI 524 matches the geometry of a representative adult head and includes all anatomy above an Axial→Cor plane inferior to the brain as indicated by line 526. The optimization required a minimum mean $B_0$ of 75 mT, and constrained all magnetic dipole moment vector magnitudes be less than that of a 1"×1"×1" block of N53 magnet material. The optimization used an initial guess solution. For example, the optimization may use used a "test-tube magnet" as an initial guess solution. In this optimization, each magnet block in the assembly was modeled as an ideal point dipole source. Next, each dipole moment vector in the optimized solution was uniformly scaled up until the dipole moment with the largest magnitude matched that of a 1"×1"×1" block of N52-grade NdFeB material. A design was then generated consisting of N=296 non-intersecting N52 magnet blocks of differing volume, such that each block's magnetic dipole moment matched that generated by the numerical optimization.

In an embodiment, a whole-brain MRI system includes a magnet that is optimized for a head-shaped region, has a mean $B_0$ field of 84.3 mT and range of 2.7 mT across the ROI, weighs 24.1 kg, and is 35×36×36 cm in size. The magnet may be constructed by approximating each dipole moment value as a physically-realizable combination of magnetic blocks of different size and material. The magnetic blocks may then be glued into a magnet former. The MRI system also includes the required RF and gradient encoding hardware.

Computer-executable instructions for optimizing the design of a portable magnet and MRI system and for operating a portable MRI system according to the above-described methods may be stored on a form of computer readable media. Computer readable media includes volatile and nonvolatile, removable, and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital volatile disks (DVD) or other optical storage, magnetic cassettes, magnetic tape, magnetic disk storage or other magnetic storage devices, or any other medium which can be used to store the desired instructions and which may be accessed by a system (e.g., a computer), including by internet or other computer network form of access The present invention has been described in terms of one or more preferred embodiments, and it should be appreciated that many equivalents, alternatives, variations, and modifications, aside from those expressly states, are possible and within the scope of the invention.

The invention claimed is:

1. A magnet assembly for a portable magnetic resonance imaging (MRI) system, the magnet assembly comprising:
   a former having a plurality of slots; and
   a plurality of magnet blocks configured to create a single-sided permanent magnet, each of the plurality of magnet blocks positioned in one of the plurality of slots of the former, wherein the arrangement of the plurality of magnet blocks is configured to optimize homogeneity over a target field of view for brain imaging and to form a cap-shaped configuration to be positioned on a head of a subject, wherein the plurality of magnet blocks comprises a plurality of magnet block size and material combinations.

2. The magnet assembly according to claim 1, wherein a weight of the magnet assembly is less than 7 kg.

3. The magnet assembly according to claim 1, wherein the magnet assembly is configured to be hand-held.

4. The magnet assembly according to claim 1, wherein the target field of view is 3 cm×8 cm×8 cm.

5. The magnet assembly according to claim 1, wherein the arrangement of the plurality of magnet blocks is further configured to generate a gradient for slice selection or readout encoding.

6. The magnet assembly according to claim 1, wherein the arrangement of the plurality of magnet blocks generates a sensitive volume that extends 3 cm beneath a surface of the subject.

7. The magnet assembly according to claim 1, wherein the cap-shaped configuration includes an inner curved surface and an outer curved surface.

8. A portable magnetic resonance imaging (MRI) assembly comprising:
   a magnet assembly comprising a plurality of magnet blocks configured to create a single-sided permanent magnet, the magnet assembly having an inner surface and an outer surface, wherein the arrangement of the plurality of magnet blocks is configured to optimize homogeneity over a target field of view for brain imaging and to form a cap-shaped configuration to be positioned on a head of a subject, wherein the plurality of magnet blocks comprises a plurality of magnet block size and material combinations;
   a set of gradient coils disposed around the outer surface of the magnet assembly and having a cap-shaped configuration; and
   an RF coil disposed inside the inner surface of the magnet assembly and having a cap-shaped configuration.

9. The portable MRI assembly according to claim 8, further comprising a controller coupled to the magnet assembly, the set of gradient coils, and the RF coil.

10. The portable MRI system according to claim 8, wherein a weight of the magnet assembly is less than 7 kg.

11. The portable MRI system according to claim 8, wherein a weight of the portable MRI system is less than 10 kg.

12. The portable MRI system according to claim 8, wherein the portable MRI system is configured to be hand-held.

13. The portable MRI system according to claim 8, further comprising:
   a housing disposed around the magnet assembly, the set of gradient coils, and the RF coil; and
   an articulated arm coupled to the housing.

14. The portable MRI system according to claim 8, wherein the target field of view is 3 cm×8 cm×8 cm.

15. The portable MRI system according to claim 8, wherein the arrangement of the plurality of magnet blocks is further configured to generate a gradient for slice selection or readout encoding.

16. The portable MRI system according to claim 8, wherein the arrangement of the plurality of magnet blocks generates a sensitive volume that extends 3 cm beneath a surface of the subject.

17. The portable MRI system according to claim 8, wherein the portable MRI system is configured to acquire three dimensional images.

18. The portable MRI system according to claim 8, wherein the inner surface of the magnet assembly is curved and the outer surface of the magnet assembly is curved.

* * * * *